United States Patent [19]

Berg et al.

[11] Patent Number: 4,551,207
[45] Date of Patent: Nov. 5, 1985

[54] SEPARATION OF ISOPROPYL ETHER FROM ACETONE BY EXTRACTIVE DISTILLATION

[76] Inventors: Lloyd Berg, 1314 S. Third Ave.; An-I Yeh, 709 S. 12th Ave., both of Bozeman, Mont. 59715

[21] Appl. No.: 576,545

[22] Filed: Feb. 3, 1984

Related U.S. Application Data

[62] Division of Ser. No. 456,321, Jan. 6, 1983, Pat. No. 4,459,179.

[51] Int. Cl.⁴ .................. B01D 3/40; C07C 41/42; C07C 45/83
[52] U.S. Cl. .................................. 203/56; 203/60; 203/64; 568/411; 568/699
[58] Field of Search .................. 203/51, 56, 57, 60, 203/58, 64, 65; 568/411, 699

[56] References Cited

U.S. PATENT DOCUMENTS

| 2,273,923 | 2/1942 | Bludworth | 203/64 |
| 2,570,205 | 10/1951 | Carlson et al. | 203/58 |
| 3,955,939 | 5/1976 | Sommer et al. | 568/896 |
| 4,012,289 | 3/1977 | Haskell | 203/51 |
| 4,459,178 | 7/1984 | Berg et al. | 203/60 |
| 4,459,179 | 7/1984 | Berg et al. | 203/57 |
| 4,469,491 | 9/1984 | Finkel | 203/64 |

FOREIGN PATENT DOCUMENTS 1020351  2/1953  France .................. 203/64

Primary Examiner—Wilbur Bascomb

[57] ABSTRACT

Isopropyl ether cannot be completely removed from isopropyl ether-acetone mixtures by distillation because of the presence of the minimum binary azeotrope. Isopropyl ether can be readily removed from mixtures containing it and acetone by using extractive distillation in which the extractive distillation agent is a higher boiling oxygenated, nitrogenous and/or sulfur containing compound or a mixture of these. Typical examples of effective agents are: dimethylsulfoxide; sulfolane and propylene glycol; adiponitrile, glycerine and ethylene glycol.

3 Claims, No Drawings

SEPARATION OF ISOPROPYL ETHER FROM ACETONE BY EXTRACTIVE DISTILLATION

This application is a division of copending application Ser. No. 456,321, filed Jan. 6, 1983, now U.S. Pat. No. 4,459,179 issued on July 10, 1984.

FIELD OF THE INVENTION

This invention relates to a method for separating isopropyl ether from acetone using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the colummn and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

One of the commercially important ways to manufacture acetone is by the catalytic dehydrogenation of isopropanol. Since the acetone (b.p.=56.15° C.) does not form an azeotrope with isopropanol (b.p.=82.4° C.), the acetone is relatively easy to separate from the unreacted isopropanol by rectification. However a concurrent reaction takes place in which some of the isopropanol dehydrates to form isopropyl ether (b.p.=69° C.). Acetone and isopropyl ether form a minimum azeotrope boiling at 54.2° C. at one Atm. pressure and containing 61 wt. % acetone, 39 wt. % isopropyl ether. It is therefore impossible to produce pure acetone from acetone-isopropyl ether mixtures by rectification because the lower boiling azeotrope will always come off overhead as the initial product. Any mixture of acetone and isopropyl ether subjected to rectification at one atomosphere pressure will produce an overhead product boiling at 54.2° C. and containing 61% acetone, 39% isopropyl ether. Extractive distillation would be an attractive method of effecting the separation of acetone from isopropyl ether if agents can be found that (1) will break the acetone-isopropyl ether azeotrope and (2) are easy to recover from the acetone, that is, form no azeotrope with acetone and boil sufficiently above acetone to make the separation by rectification possible with only a few theoretical plates.

Extractive distillation typically requires the addition of an equal amount to twice as much extractive agent as the acetone-isopropyl ether on each plate in the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with acetone otherwise it will form a two phase azeotrope with the acetone in the recovery column and some other method of separation will have to be employed.

The breaking of an azeotrope by extractive distillation is a new concept. The closest applicaiton of this concept might be the breaking of the ethanol-water azeotrope. J. Schneible, (U.S. Pat. No. 1,469,447) used glycerol; P. V. Smith and C. S. Carlson (U.S. Pat. No. 2,559,519) employed ethoxyethanol and butoxyethanol for this purpose and W. E. Catterall, (U.S. Pat. No. 2,591,672) reported gasoline as being effective. These are dehydrations and operate more conventionally as a solvent extraction process rather than an extractive distillation.

OBJECTIVE OF THE INVENTION

The object of this invention is to provide a process or method of extractive distillation that will enhance the relative volatility of isopropyl ether from acetone in their separation in a rectification column. It is a further object of this invention to identify suitable extractive distillation agents which will eliminate the isopropyl ether-acetone binary azeotrope and make possible the production of pure isopropyl ether and acetone by rectification. It is a further object of this invention to identify organic compounds which, in addition to the above constraints, are stable, can be separated from acetone by rectification with relatively few plates and can be recycled to the extractive distillation column and reused with little decomposition.

SUMMARY OF THE INVENTION

The objects of this invention are provided by a process for separating isopropyl ether from acetone which entails the use of certain oxygenated, nitrogenous and/or sulfur containing organic compounds as the agent in extractive distillation.

DETAILED DESCRIPTION OF THE INVENTION

We have discovered that cetain oxygenated, nitrogenous and/or sulfur containing organic compounds, some individually but principally as mixtures, will effectively negate the isopropyl ether-acetone azeotrope and permit the separation of pure isopropyl ether from acetone by rectification when employed as the agent in extractive distillation. Table I lists the compounds, mixtures and approximate proportions that we have found to be exceptionally effective. Table II lists the compounds, mixtures and approximate proportions that are successful but do not give quite as high a relative volatility as that obtained from those in Table I. The data in Tables I and II were obtained in a vapor-liquid equilibrium still. In each case, the starting material was the isopropyl ether-acetone azeotrope. The ratios are the parts by weight of extractive agent used per part of isopropyl ether-acetone azeotrope. The relative volatilities are listed for each of the two ratios employed.

The compounds that are effective as extractive distillation agents when used alone are dimethylsulfoxide, sulfolane, dimethylformamide and adiponitrile. The compounds which are effective when used in mixtures of two or more components are diethylene glycol, dipropylene glycol, 1,5-pentanediol, hexylene glycol, polyethylene glycol, diisooctyl phthalate, benzyl alcohol, phenol and nitrobenzene.

The ratios shown in Tables I, and II are the parts by weight of extractive agent used per part of isopropyl ether-acetone azeotrope. The two relative volatilities correspond to the two different ratios. For example in Table I, one part of adiponitrile with one part of isopropyl ether-acetone azeotrope gives a relative volatility of 3.82, 6/5 parts of adiponitrile gives 4.07. One half part of glycerine mixed with one half part of sulfolane with one part of isopropyl ether-acetone azeotrope gives a relative volatility of 3.85, 3/5 parts of glycerine plus 3/5 parts of sulfolane gives 4.36. One third parts of glycerine plus ⅓ part of ethylene glycol plus ⅓ parts of DMSO mixed with one part of isopropyl ether-acetone azeotrope gives a relative volatility of 4.82, with 2/5 parts, these three give 4.05.

In every example in Tables I, and II the starting material is the isopropyl ether-acetone azeotrope which possesses a relative volatility of 1.00.

Several of the compounds and mixtures listed in Tables I and II and whose relative volatility had been determined in the vapor-liquid equilibrium still, were then evaluated in a glass perforated plate rectification column possessing 4.5 theoretical plates. The results are listed in Table III. The isopropyl ether-acetone mixture studied contained 8% isopropyl ether, 92% acetone. The isopropyl ether-acetone azeotrope contains 39 wt. % isopropyl ether, 61 wt. % acetone. What is truly remarkable here is that isopropyl ether, the less volatile component, will come off as overhead product. In every case the feed or bottoms composition contained less than 39% isopropyl ether and in every case the overhead is richer than 39% isopropyl ether. Without the extractive agent, the overhead would be the azeotrope, 39% isopropyl ether. This proves that the extractive agent is negating the azeotrope and makes the rectification proceed as if the azeotrope no longer existed and brings the less volatile component, isopropyl ether, out as the overhead. It is our belief that this is the first time that this has been accomplished for any azeotrope.

The data in Table III was obtained in the following manner. The charge designated "blank" was 8% isopropyl ether, 92% acetone and after 1.5 hours operation in the 4.5 theoretical plate column, the relative volatility of the separation between the isopropyl ether-acetone azeotrope and acetone was 1.42. The remaining data is for the extractive distillation agents designated. Here we not only have negated the azeotrope but the isopropyl ether has become the more volatile component. The temperature of the overhead approaches 63° C., the boiling point of pure isopropyl ether at 630 mm.Hg and the acetone goes to the stillpot with the extractive distillation agent. The designation "R" by the extractive distillation agent means that the same material was recovered and re-used to show its stability in repeated operation. When the acetone-extractive distillation agent mixture taken from the stillpot is redistilled, acetone comes off overhead in the usual way at its normal boiling point, 56° C.

TABLE I

Extractive Distillation Agents Which Are Exceptionally Effective In Separating Isopropyl Ether From Acetone.

| Compounds | Ratios | Relative Volatilities |
|---|---|---|
| Dimethylsulfoxide (DMSO) | 1 6/5 | 3.78 4.92 |
| Adiponitrile | " | 3.82 4.07 |
| Sulfolane | " | 3.09 3.80 |
| Glycerine, DMSO | (½)² (3/5)² | — 3.82 |
| Glycerine, Dimethylformamide (DMFA) | " | 2.91 3.63 |
| Glycerine, Sulfolane | " | 3.85 4.36 |
| Ethylene glycol, DMSO | " | 3.14 3.31 |
| Ethylene glycol, Sulfolane | " | 4.01 4.57 |
| DMSO, Adiponitrile | " | 3.71 3.81 |
| DMSO, 1,4-Butanediol | " | 3.08 3.50 |
| DMSO, 3-Chloro-1,2-propanediol | " | 2.74 4.73 |
| Sulfolane, Adiponitrile | " | 3.98 3.08 |
| Sulfolane, DMSO | " | 3.57 4.10 |
| Sulfolane, Propylene glycol | " | 3.07 3.16 |
| Sulfolane, Triethylene glycol | " | 3.07 3.10 |
| Sulfolane, 1,6-Hexanediol | " | 3.56 4.34 |
| Sulfolane, 3-Chloro-1,2-propanediol | " | 3.07 3.29 |
| Glycerine, Ethylene glycol, DMSO | (⅓)³ (2/5)³ | 4.82 4.05 |
| Glycerine, Ethylene glycol, Adiponitrile | " | 4.04 4.60 |
| Glycerine, Ethylene glycol, Sulfolane | " | 3.60 3.06 |
| Glycerine, Propylene glycol, DMSO | " | 2.93 3.59 |
| Glycerine, 1,4-Butanediol, DMSO | " | 3.46 3.40 |
| Glycerine, Tetraethylene glycol, DMSO | " | 3.70 3.98 |
| Glycerine, Polyethylene glycol 300, DMSO | " | 3.60 4.36 |
| Glycerine, 3-Chloro-1,2-propanediol, DMSO | " | 3.20 3.64 |
| Glycerine, Diisooctyl phthalate, DMSO | " | 3.95 3.13 |

TABLE I-continued

Extractive Distillation Agents Which Are Exceptionally Effective In Separating Isopropyl Ether From Acetone.

| Compounds | Ratios | Relative Volatilities |
|---|---|---|
| Glycerine, Adiponitrile, DMSO | " | 4.19 4.00 |
| Glycerine, Sulfolane, DMSO | " | 3.84 3.79 |
| Ethylene glycol, Propylene glycol, DMSO | " | 4.03 3.66 |
| Ethylene glycol, 1,4-Butanediol, DMSO | " | 2.98 3.47 |
| Ethylene glycol, 1,5-Pentanediol, DMSO | " | 3.12 3.42 |
| Ethylene glycol, Diethylene glycol, DMSO | " | 3.21 3.34 |
| Ethylene glycol, Triethylene glycol, DMSO | " | 3.04 3.83 |
| Ethylene glycol, Tetraethylene glycol, DMSO | " | 3.30 3.54 |
| Ethylene glycol, 3-Chloro-1,2-propanediol, DMSO | " | 3.01 3.87 |
| Ethylene glycol, Adiponitrile, DMSO | " | 3.80 4.39 |
| Ethylene glycol, Sulfolane, DMSO | " | 4.23 6.39 |
| Sulfolane, Propylene glycol, DMSO | " | 3.17 3.53 |
| Sulfolane, 1,4-Butanodiol, DMSO | " | 4.88 — |
| Sulfolane, Adiponitrile, DMSO | " | 3.46 3.32 |
| DMSO, Sulfolane, Adiponitrile, Glycerine | $(\frac{1}{4})^4 (\frac{1}{4})^4$ | 4.38 4.32 |
| DMSO, Sulfolane, Adiponitrile, Ethylene glycol | " | 4.53 5.04 |
| DMSO, Sulfolane, Adiponitrile, Propylene glycol | " | 3.60 3.80 |
| DMSO, Sulfolane, Adiponitrile, 1,5-Pentanediol | " | 2.96 3.27 |
| DMSO, Sulfolane, Adiponitrile, 1,6-Hexanediol | " | 3.01 3.10 |
| DMSO, Sulfolane, Adiponitrile, Diethylene glycol | " | 3.24 3.28 |
| DMSO, Sulfolane, Adiponitrile, Triethylene glycol | " | 3.57 3.55 |
| DMSO, Sulfolane, Adiponitrile, Tetraethylene glycol | " | 3.27 3.20 |
| DMSO, Sulfolane, Adiponitrile, Dipropylene glycol | " | 2.87 3.17 |
| DMSO, Sulfolane, Adiponitrile, 3-Cl—1,2-propanediol | " | 3.16 3.38 |

TABLE II

Extractive Distillation Agents Which Are Effective In Separating Isopropyl Ether From Acetone.

| Compounds | Ratios | Relative Volatilities |
|---|---|---|
| Dimethylformamide (DMFA) | 1 (6/5) | 2.05 2.08 |
| DMSO, Propylene glycol | $(\frac{1}{2})^2 (3/5)^2$ | 2.68 2.74 |
| DMSO, 1,3-Butanediol | " | 2.76 2.38 |
| DMSO, 1,5-Pentanediol | " | 2.37 2.70 |
| DMSO, 1,6-Hexanodiol | " | 1.74 2.51 |
| DMSO, Hexylene glycol | " | 2.01 2.04 |
| DMSO, Diethylene glycol | " | 2.41 3.23 |
| DMSO, Triethylene glycol | " | 2.57 2.86 |
| DMSO, Tetraethylene glycol | " | 2.56 2.78 |
| DMSO, Dipropylene glycol | " | 2.36 2.45 |
| DMSO, 3-Chloro-1,2-propanediol | " | 2.53 2.87 |
| DMSO, Benzyl alcohol | " | 2.19 3.00 |
| Sulfolane, 1,3-Butanediol | " | 2.79 2.99 |
| Sulfolane, 1,4-Butanediol | " | 2.83 3.05 |
| Sulfolane, 1,5-Pentanediol | " | 2.56 2.74 |
| Sulfolane, Diethylene glycol | " | 2.93 2.82 |
| Sulfolane, Tetraethylene glycol | " | 2.87 2.93 |
| Sulfolane, Dipropylene glycol | " | 2.47 2.85 |
| Sulfolane, Phenol | " | 2.32 2.63 |
| DMFA, 1,3-Butanediol | " | 2.52 2.55 |
| DMFA, 3-Chloro-1,2-propanediol | " | 2.29 2.38 |
| Sulfolane, 1,6-Hexanediol | " | 2.51 2.83 |
| Sulfolane, Hexylene glycol | " | 2.11 2.16 |
| Formamide, Glycerine, Ethylene glycol | $(\frac{1}{3})^3 (2/5)^3$ | 2.48 2.98 |
| DMSO, Glycerine, Propylene glycol | " | 2.97 2.13 |
| DMSO, Glycerine, 1,3-Butanediol | " | 2.95 1.95 |
| DMSO, Glycerine, 1,5-Pentanediol | " | 2.56 3.40 |
| DMSO, Glycerine, 1,6-Hexanediol | " | 2.37 2.93 |
| DMSO, Glycerine, Hexylene glycol | " | 2.44 2.70 |
| DMSO, Glycerine, Triethylene glycol | " | 2.33 2.00 |
| DMSO, Glycerine, Diethylene glycol | " | 2.60 3.37 |
| DMSO, Glycerine, Dipropylene glycol | " | 2.40 2.76 |
| DMSO, Glycerine, 3-Chloro-1,2-propanediol | " | 2.26 2.87 |
| DMSO, Glycerene, Nitrobenzene | " | 3.36 2.11 |
| DMFA, Glycerine, 1,5-Pentanediol | " | 2.21 3.25 |
| DMSO, Ethylene glycol, 1,3-Butanediol | " | 2.60 3.38 |
| DMSO, Ethylene glycol, 1,6-Hexanediol | " | 2.33 3.09 |
| DMSO, Ethylene glycol, Hexylene glycol | " | 2.42 2.65 |
| DMSO, Ethylene glycol, Dipropylene glycol | " | 2.45 3.18 |
| DMSO, Ethylene glycol, Polyethylene glycol 300 | " | 2.73 2.90 |
| DMSO, Propylene glycol, 3-Chloro-1,2-propanediol | " | 2.38 2.19 |
| DMSO, Sulfolane, Adiponitrile, 1,4-Butanediol | $(\frac{1}{4})^4 (\frac{1}{4})^4$ | 2.92 2.82 |
| DMSO, Sulfolane, Adiponitrile, Hexylene glycol | " | 2.32 2.49 |

TABLE III

Data From Runs Made in Rectification Column.

| Compounds | Overhead Temp., °C. | Stillpot Temp., °C. at Start | Stillpot Temp., °C. After 1.5 hrs. | Relative Volatilty | Time to Reach Equil., hrs. |
| --- | --- | --- | --- | --- | --- |
| Blank | 49 | 53 | 53 | 1.42 | 0.5 |
| DMSO | 63 | 54 | 86 | 5.97 | 1 |
| DMSO (R) | 63 | 54 | 84 | 5.90 | 1 |
| Adiponitrile | 62 | 54 | 85 | 5.43 | 1 |
| Sulfolane | 62 | 54 | 84 | 4.52 | 1 |
| Sulfolane (R) | 59 | 55 | 84 | 4.43 | 1 |
| DMSO + Adiponitrile | 62 | 54 | 87 | 4.89 | 1 |
| DMSO (R) + Sulfolane (R) | 62 | 54 | 84 | 4.62 | 1 |
| Sulfolane (R) + Adiponitrile (R) | 61 | 55 | 82 | 4.27 | 1 |
| DMSO + Glycerine | 57 | 56 | 70 | 2.89 | 1 |
| Sulfolane + Glycerine | 56 | 55 | 76 | 2.74 | 1 |
| DMSO (R) + Sulfolane (R) + Adiponitrile (R) | 61 | 55 | 83 | 4.06 | 1 |
| DMSO (R) + Sulfolane (R) + Glycerine (R) | 60 | 55 | 76 | 3.19 | 1 |

THE USEFULNESS OF THE INVENTION

The usefulness or utility of this invention can be demonstrated by referring to the data presented in Tables I, II, and III. All of the successful extractive distillation agents show that isopropyl ether can be removed from its binary minimum azeotrope with acetone by means of distillation in a rectification column and that the ease of separation as measured by relative volatility is considerable. Without these extractive distillation agent, no improvement above the azeotrope composition will occur in the rectification column. The data also show that the most attractive agents will operate at a boilup rate low enough to make this a useful and efficent method of recovering high purity isopropyl ether from any mixture with acetone including the minimum azeotrope. The stability of the compounds used and the boiling point difference is such that complete recovery and recycle is obtainable by a simple distillation and the amount required for make-up is small.

WORKING EXAMPLES

Example 1

The isopropyl ether-acetone azeotrope is 39% isopropyl ether, 61% acetone. Fifty grams of the isopropyl ether-acetone azeotrope and fifty grams of sulfolane were charged to an Othmer type glass vapor-liquid equilibrium still and refluxed for ten hours. Analysis of the vapor and liquid by gas chromatography gave vapor 71.4% isopropyl ether, 28.6% acetone; liquid of 44.7% isopropyl ether, 55.3% acetone. This indicates a relative volatility of of 3.09.

Ten grams of sulfolane were added and refluxing continued for another eleven hours. Analysis indicated a vapor composition of 71.1% isopropyl ether, 28.9% acetone, a liquid composition of 39.2% isopropyl ether, 60.8% acetone which is a relative volatility of 3.80.

Example 2

Fifty grams of isopropyl ether-acetone azeotrope, 25 grams of sulfolane and 25 grams of DMSO were charged to the vapor-liquid equilibrium still and refluxed for ten hours. Analysis indicated a vapor composition of 70.5% isopropyl ether, 29.5% acetone, a liquid composition of 42% isopropyl ether, 58% acetone which is a relative volatility of 3.57. Five grams of sulfolane and five grams of DMSO were added and refluxing continued for another twelve hours. Analysis indicated a vapor composition of 71.7% isopropyl ether, 28.3% acetone, a liquid composition of 38.2% isopropyl ether, 61.8% acetone which is a relative volatility of 4.10.

Example 3

Fifty grams of the isopropyl ether-acetone azeotrope, 17 grams of glycerine, 17 grams of DMSO and 17 grams of sulfolane were charged to the vapor-liquid equilibrium still and refluxed for ten hours. Analysis indicated a vapor composition of 69.9% isopropyl ether, 30.1% acetone, a liquid composition of 37.7% isopropyl ether, 62.3% acetone which is a relative volatility of 3.84. Three grams each of glycerine, DMSO and sulfolane were added and refluxing continued for another twelve hours. Analysis indicated a vapor composition of 69.5% isopropyl ether, 30.5% acetone, a liquid composition of 37.5% isopropyl ether, 62.5% acetone which is a relative volatility of 3.79.

Example 4

A glass perforated plate rectification column was calibrated with ethylbenzene and p-xylene which possesses a relative volatility of 1.06 and found to have 4.5 theoretical plates. A solution of 460 grams of acetone and 40 grams of isopropyl ether was placed in the stillpot and heated. When refluxing began, an extractive agent containing pure sulfolane was pumped into the column at a rate of 20 ml/min. The temperature of the extractive agent as it entered the column was 52° C. After establishing the feed rate of the extractive agent, the heat input to the isopropyl ether and acetone in the stillpot was adjusted to give a total reflux rate of 10–20 ml/min. After one-half hour of operation, overhead and bottoms samples of approximately two ml. were collected and analysed using gas chromatography. The overhead analysis was 91.25% isopropyl ether, 8.75% acetone. The bottoms analysis was 4.68% isopropyl ether, 95.32% acetone. Using these compositions in the Fenske equation, with the number of theoretical plates in the column being 4.5, gave an average relative volatility of 3.29 for each theoretical plate. After one hour of total operating time, the overhead and bottoms samples were again taken and analysed. The overhead composition was 96.68% isopropyl ether, 3.32% acetone and the bottoms composition was 3.15% isopropyl ether, 96.85% acetone. This gave an average relative volatility of 4.53 for each theoretical plate. After 1.5 hours of total operating time, the overhead and bottoms samples were again taken and analysed. The overhead composition was 96.46% isopropyl ether, 3.54% acetone and the bottoms composition was 2.97% isopropyl ether, 97.03% acetone. This gave an average relative volatility of 4.52 for each theoretical plate.

Example 5

A solution of 460 grams of acetone and 40 grams of isopropyl ether was placed in the stillpot of the same column used in Example 4 and heat applied. When refluxing began, an extractive agent of 50% DMSO and 50% sulfolane was fed into the top of the column at a feed rate of 20 ml/min. and a temperature of 52° C. After establishing the feed rate of the extractive agent, the heat input to the isopropyl ether and acetone in the stillpot was adjusted to give a total reflux rate of 10–20 ml/min. Having established the reflux rate, the column was allowed to operate for one-half hour. After one-half hour of steady operation, overhead and bottoms samples of approximately two ml. were collected and analysed using gas chromatography. The overhead analysis was 89.07% isopropyl ether, 10.93% acetone; the bottoms analysis was 4.65% isopropyl ether, 95.35% acetone. Using these compositions in the Fenske equation with the the number of theoretical plates of the column being 4.5, gave an average relative volatility of 3.12 for each theoretical plate. After one hour of total operation, the overhead composition was 96.95% isopropyl ether, 3.05% acetone and the bottoms composition was 3.13% isopropyl ether, 96.87% acetone. This gave an average relative volatility of 4.62 for each theoretical plate. After 1.5 hours of total operation, the overhead composition was 97.96% isopropyl ether, 2.04% acetone and the bottoms composition was 3.5% isopropyl ether, 96.5% acetone. This gave an average relative volatility of 4.94 for each theoretical plate.

We have shown that by the use of the proper compound or combination of compounds as agents isopropyl ether can be effectively removed from its mixture with acetone in any proportion including the minimum azeotrope.

The nature of the present invention having been described, what we wish to claim as new and useful and secure by Letters Patent is:

1. A method for recovering isopropyl ether from a mixture of isopropyl ether and acetone which comprises distilling a mixture of isopropyl ether and acetone in a rectification column in the presence of an effective amount of an extractive agent, recovering essentially pure isopropyl ether as overhead product and obtaining the extractive agent and acetone from the stillpot or reboiler, the extractive agent comprises at least adiponitrile.

2. A method for recovering isopropyl ether from a mixture of isopropyl ether and acetone which comprises distilling a mixture of isopropyl ether and acetone in a rectification column in the presence of an effective amount of an extractive agent, recovering essentially pure isopropyl ether as overhead product and obtaining the extractive agent and acetone from the stillpot or reboiler, the extractive agent comprises at least dimethylformamide.

3. The method of claim 2 in which the extractive agent comprises dimethylformamide and at least one material from the group consisting of 1,3-butanediol, 1,5-pentanediol and 3-chloro-1,2-propanediol.

* * * * *